United States Patent
Wellington et al.

(10) Patent No.: US 9,245,305 B2
(45) Date of Patent: Jan. 26, 2016

(54) SYSTEM AND METHOD FOR PROVIDING INFORMATION REGARDING A STATUS OF AN ITEM

(75) Inventors: Robert J. Wellington, Pittsburgh, PA (US); Brian R. Curren, Wexford, PA (US); David G. Wolfe, Wexford, PA (US); Kevin F. Seip, Richboro, PA (US)

(73) Assignee: Aethon, Inc., Pittsburgh, PA (US)

( * ) Notice: Subject to any disclaimer, the term of this patent is extended or adjusted under 35 U.S.C. 154(b) by 218 days.

(21) Appl. No.: 12/962,528

(22) Filed: Dec. 7, 2010

(65) Prior Publication Data

US 2011/0137759 A1 Jun. 9, 2011

Related U.S. Application Data

(60) Provisional application No. 61/267,414, filed on Dec. 7, 2009.

(51) Int. Cl.
*G06Q 10/06* (2012.01)
*G06Q 10/08* (2012.01)
*G06Q 50/22* (2012.01)

(52) U.S. Cl.
CPC .............. *G06Q 50/22* (2013.01); *G06Q 10/06* (2013.01); *G06Q 10/087* (2013.01); *G06Q 10/0833* (2013.01)

(58) Field of Classification Search
None
See application file for complete search history.

(56) References Cited

U.S. PATENT DOCUMENTS

| | | | |
|---|---|---|---|
| 7,118,036 B1* | 10/2006 | Couch et al. | 235/385 |
| 7,142,118 B2* | 11/2006 | Hamilton et al. | 340/572.1 |
| 8,068,023 B2* | 11/2011 | Dulin et al. | 340/539.13 |
| 8,164,451 B2* | 4/2012 | Nichols et al. | 340/568.7 |
| 2002/0041234 A1* | 4/2002 | Kuzma et al. | 340/572.8 |
| 2003/0160698 A1* | 8/2003 | Andreasson et al. | 340/573.1 |
| 2004/0257231 A1* | 12/2004 | Grunes et al. | 340/572.1 |
| 2005/0234641 A1* | 10/2005 | Marks et al. | 701/213 |
| 2007/0129849 A1* | 6/2007 | Zini et al. | 700/258 |
| 2008/0316045 A1* | 12/2008 | Sriharto et al. | 340/825.49 |
| 2009/0160646 A1* | 6/2009 | Mackenzie et al. | 340/572.1 |
| 2011/0047183 A1* | 2/2011 | Ford et al. | 707/783 |

OTHER PUBLICATIONS

"P2S2 Tracking Services User Manual", Aug. 9, 2007.*
"Tracking with fedex.com just got easier!", snapshot taken, Jan. 24, 2009, available at https://web.archive.org/web/20090124223157/http://offer.van.fedex.com/m/p/fdx/new/online_tracking.asp?.*
Schneegans, Sebastian, Philipp Vorst, and Andreas Zell. "Using RFID Snapshots for Mobile Robot Self-Localization." EMCR. 2007.*

* cited by examiner

*Primary Examiner* — Allen Chein
(74) *Attorney, Agent, or Firm* — Buchanan Ingersoll & Rooney PC

(57) ABSTRACT

A system. A system includes a computing system. The computing system includes a processor, a first module, a second module, and a third module. The first module is communicably connected to the processor and is configured for receiving chain of custody information associated with an item. The second module is communicably connected to the processor and is configured for determining a status of the item based on the received chain of custody information. The third module is communicably connected to the processor and is configured for arranging data into a specified format. The data includes the status of the item and the chain of custody information. The third module is also configured for transmitting the data.

21 Claims, 17 Drawing Sheets

Chain of Custody

| Current Deliveries | | | |
|---|---|---|---|
| Medication: Hydromorphone PCA 2mg/ml<br>Destination: 3S<br>TUG: TUG 3 | | | |

| | Reset Deliveries | | |
|---|---|---|---|
| | Status | Staff Member | Time |
| | Delivery Created | Debora Parker | 9:25 AM |
| | Loaded Into Drawer | Joshua Parnell | 9:26 AM |
| | Sent from Pharmacy | Joshua Parnell | 9:28 AM |
| | Estimate Arrival Time | | 9:57 AM (13 minutes) |

FIG. 8

Chain of Custody

Current Deliveries

Medication: Hydromorphone PCA 20mg/ml
Destination: 5E Lock Box
TUG: TUG 4

| Status | Staff Member | Time |
|---|---|---|
| Delivery Created | Dustin Bowers | 9:05 AM |
| Loaded Into Drawer | Debora Parker | 9:06 AM |
| Sent from Pharmacy | Debora Parker | 9:06 AM |
| Received at 5E | Jeannie McNeal | 9:19 AM |

Medication: Cefazoin 1g syringe
Destination: 4S Refrigerator
TUG: TUG 2

| Status | Staff Member | Time |
|---|---|---|
| Delivery Created | Mike Anderson | 8:58 AM |
| Loaded Into Drawer | Joshua Parnell | 9:01 AM |
| Sent from Pharmacy | Joshua Parnell | 9:02 AM |
| Estimate Arrival Time | Shirley Belles | 9:13 AM |

Medication: Filgrastim 480mcg vial
Destination: 3N Refrigerator
TUG: TUG 1

| Status | Staff Member | Time |
|---|---|---|
| Delivery Created | Dustin Bowers | 8:49 AM |
| Loaded Into Drawer | Debora Parker | 8:50 AM |
| Sent from Pharmacy | Debora Parker | 8:52 AM |
| Received at 3N | Grace Helms | 9:03 AM |

Reset Deliveries

FIG. 9

Lock Boxes

Recent Deliveries

| Medication: | Hydromorphone PCA 20mg/ml |
|---|---|
| Destination: | 5E Lock Box |
| TUG: | TUG 4 |

Lock Box Contents

| Status | Staff Member | Time |
|---|---|---|
| Sent from Pharmacy | Debora Parker | 9:06 AM |
| Received at 5E | Jeannie McNeal | 9:19 AM |
| Stored in Lock Box | Stephanie Boyce | 9:21 AM |

| Medication: | Alprostadil 500mcg IV |
|---|---|
| Destination: | 6N Lock Box |
| TUG: | TUG 1 |

| Status | Staff Member | Time |
|---|---|---|
| Sent from Pharmacy | Dustin Bowers | 8:49 AM |
| Received at 6N | Linda Johnson | 9:03 AM |
| Stored in Lock Box | Linda Johnson | 9:05 AM |

| Medication: | Hydromorphone PCA 20mg/ml |
|---|---|
| Destination: | 3S Lock Box |
| TUG: | TUG 2 |

| Status | Staff Member | Time |
|---|---|---|
| Sent from Pharmacy | Debora Parker | 8:42 AM |
| Received at 3S | Audrey Tate | 8:55 AM |
| Stored in Lock Box | Barbara King | 8:59 AM |

Legend: Acceptable (Under 20 Minutes)  1st Alert (20-30 Minutes)  High Alert (Over 30 Minutes)

FIG. 10

Lock Boxes

| Recent Deliveries | | | Lock Box Contents | | |
|---|---|---|---|---|---|
| 3S<br>Hydromorphone PCA 20mg/ml<br>Valium 5mg tab<br>Fentanyl 75 mcg patch | 3N<br>Hycodan syrup 5ml<br>Codeine 30mg tab | | 4S<br>Alprostadil 500mcg IV<br>Keflex 500mg cap | 4NW<br>Fentanyl 75 mcg patch<br>Valium 5mg tab<br>Hycodan syrup 5ml | |
| 4N<br>Morphine 100mg/4ml<br>Keflex 500mg cap | 5E<br>Hydromorphone PCA 20mg/ml<br>Codeine 30mg tab<br>Keflex 500mg cap | | 5SE<br>Keflex 500mg cap<br>Fentanyl 75 mcg patch | 5S<br>Erythromycin 250mg tab<br>Hydromorphone PCA 20mg/ml | |
| 5SW<br>Fentanyl 75 mcg patch<br>Valium 5mg tab<br>Hycodan syrup 5ml | 5N<br>Alprostadil 500 mcg IV<br>Keflex 500mg cap | | 6S<br>Hycodan syrup 5ml<br>Codeine 30mg tab | 6N<br>Alprostadil 500mg IV<br>Hydromorphone PCA 20mg/ml<br>Valium 5mg tab<br>Fentanyl 75 mcg patch | |

FIG. 11

Refrigerators

Recent Deliveries | Refrigerator Contents

Medication: Cefazoin 1g syringe
Destination: 4S Refrigerator
TUG: TUG 2

| Status | Staff Member | Time |
|---|---|---|
| Sent from Pharmacy | Joshua Parnell | 9:02 AM |
| Received at 4S | Shirley Belles | 9:13 AM |
| Not Yet Refrigerated | | 31 Minutes Elapsed |

Medication: Filgrastim 480mcg vial
Destination: 3N Refrigerator
TUG: TUG 1

| Status | Staff Member | Time |
|---|---|---|
| Sent from Pharmacy | Debora Parker | 8:52 AM |
| Received at 3N | Grace Helms | 9:08 AM |
| Refrigerated | | 9:10 AM |

Medication: Cefazoin 1g syringe
Destination: 6N Refrigerator
TUG: TUG 4

| Status | Staff Member | Time |
|---|---|---|
| Sent from Pharmacy | Joshua Parnell | 8:47 AM |
| Received at 6N | Marian Olson | 8:59 AM |
| Refrigerated | | 9:03 AM |

Legend: Acceptable (Under 20 Minutes) 1st Alert (20-30 Minutes) High Alert (Over 30 Minutes)

FIG. 12

Refrigerators

Recent Deliveries

3S
Fentanyl 100mcg/400ml IV
Midazolam 100mg/100ml IV

3N
Filgrastim 480mcg vial
Fentanyl 2000mcg/400ml IV

4S
Midazolam 100mg/100ml IV
Filgrastim 480mcg vial
Fentanyl 2000mcg/400ml IV

4NW
Morphine 100mg/4ml
Fentanyl 1000mcg/400ml IV
Cefazoin 1g syringe
Filgrastim 480mcg vial

4N
Filgrastim 480mcg vial
Fentanyl 2000mcg/400ml IV
Midazolam 100mg/100ml IV

4NE
Fentanyl 1000mcg/400ml IV
Morphine 100mg/250ml IV

5SE
Midazolam 100mg/100ml IV
Fentanyl 1000mcg/400ml IV

5S
Cefazoin 1g syringe
Filgrastim 480mcg vial

5SW
Morphine 100mg/250ml IV
Fentanyl 100mcg/400ml IV
Cefazoin 1g syringe

5N
Cefazoin 1g syringe
Filgrastim 2000mcg/400ml IV

6S
Filgrastim 480mcg vial
Fentanyl 2000mcg/400ml IV

6N
Fentanyl 1000mcg/400ml IV
Cefazoin 1g syringe
Midazolam 100mg/100ml IV

Refrigerator Contents

FIG. 13

Pneumatic Tube System

Recent Tube Deliveries (Past 2 Hours)

Sent from Pharmacy

| Unit | Time Sent | Time of Arrival |
|---|---|---|
| 3N | 9:43 AM | In Transit |
| 3N | 8:52 AM | 8:59 AM |
| 3S | 9:18 AM | 9:25 AM |
| 3S | 9:05 AM | 9:11 AM |
| 4N | 9:41 AM | In Transit |
| 4NE | 9:31 AM | 9:38 AM |
| 4NE | 9:14 AM | 9:21 AM |
| 4NE | 8:56 AM | 9:04 AM |
| 4NW | 9:37 AM | 9:44 AM |
| 4S | 8:58 AM | 9:06 AM |
| 5S | 9:28 AM | 9:34 AM |
| 5SE | 9:40 AM | In Transit |
| 5SW | 9:22 AM | 9:29 AM |
| 6N | 9:13 AM | 9:19 AM |
| 6S | 9:36 AM | 9:42 AM |
| 6S | 9:25 AM | 9:32 AM |
| 6S | 8:47 AM | 8:54 AM |
| Endo | 9:29 AM | 9:35 AM |
| ICU | 9:34 AM | 9:40 AM |
| PACU | 9:02 AM | 9:09 AM |

Earlier Tube Deliveries Previous 8-Hours

Sent from Pharmacy

| Unit | Time Sent | Time of Arrival |
|---|---|---|
| 2N | 8:51 AM | 8:45 AM |
| 3S | 9:25 AM | 9:19 AM |
| 3S | 8:56 AM | 8:51 AM |
| 4N | 9:41 AM | 9:34 AM |
| 4NE | 9:29 AM | 9:22 AM |
| 5S | 9:24 AM | 9:17 AM |
| 6S | 9:36 AM | 9:32 AM |
| 6S | 9:19 AM | 9:12 AM |
| Endo | 9:32 AM | 9:25 AM |
| ICU | 9:07 AM | 9:00 AM |

*FIG. 14*

Automated Dispensing Cabinets

| Medication: | Diazepam 5mg tab |
|---|---|
| Patient: | Mark Harrison |
| Destination: | 2N Cabinet |
| TUG: | TUG 1 |

| Status | Staff Member | Time |
|---|---|---|
| Sent from Pharmacy | Debora Parker | 9:31 AM |
| Received at 2N | Holly Smith | 9:39 AM |
| Not Yet Stored | | 5 Minutes Elapsed |

| Medication: | Lorazepam 2mg syringe |
|---|---|
| Patient: | Chris Smith |
| Destination: | 4NE Cabinet |
| TUG: | TUG 4 |

| Status | Staff Member | Time |
|---|---|---|
| Sent from Pharmacy | Debora Parker | 8:49 AM |
| Received at 4NE | Mary Stanford | 9:00 AM |
| Not Yet Stored | | 44 Minutes Elapsed |

| Medication: | Fentanyl 75mcg patch |
|---|---|
| Patient: | Susan Jennings |
| Destination: | 5S Cabinet |
| TUG: | TUG 3 |

| Status | Staff Member | Time |
|---|---|---|
| Sent from Pharmacy | Dustin Bowers | 8:43 AM |
| Received at 5S | Cindy Harrison | 8:54 AM |
| Stored in Cabinet | Cindy Harrison | 8:57 AM |

Legend: Acceptable (Under 20 Minutes) 1st Alert (20-30 Minutes) High Alert (Over 30 Minutes)

FIG. 15

Robot/Carousel

| Medication: | Lorazepam 1mg tab | Status | Staff Member | Time |
|---|---|---|---|---|
| Destination: | 5S | Picked | Robot | 8:55 AM |
| TUG: | TUG 3 | Loaded Into TUG | Debora Parker | 8:58 AM |
| | | Sent from Pharmacy | Debora Parker | 8:59 AM |
| | | Received at 5S | Cathy Temple | 9:14 AM |

| Medication: | Alprazolam 0.25mg tab | Status | Staff Member | Time |
|---|---|---|---|---|
| Destination: | 3N | Picked | Carousel | 8:47 AM |
| TUG: | TUG 1 | Loaded Into TUG | Debora Parker | 8:50 AM |
| | | Sent from Pharmacy | Debora Parker | 8:52 AM |
| | | Received at 3N | Grace Helms | 9:08 AM |

| Medication: | Daptomycin 420mg IV | Status | Staff Member | Time |
|---|---|---|---|---|
| Destination: | 4NW | Picked | Carousel | 8:45 AM |
| TUG: | TUG 4 | Loaded Into TUG | Joshua Parnell | 8:47 AM |
| | | Sent from Pharmacy | Joshua Parnell | 8:48 AM |
| | | Received at 4NW | Elizabeth Spencer | 8:55 AM |

*FIG. 16*

SYSTEM AND METHOD FOR PROVIDING INFORMATION REGARDING A STATUS OF AN ITEM

CROSS-REFERENCE TO RELATED APPLICATION

This application claims the benefit under 35 U.S.C. §119 (e) of the earlier filing date of U.S. Provisional Patent Application No. 61/267,414 filed on Dec. 7, 2009.

BACKGROUND

This application discloses an invention which is related, generally and in various embodiments, to a system and method for providing information regarding a status of an item. The information may be provided for a variety of different items, and may relate to items being transported from a first location within an environment to a second location within the environment. For purposes of simplicity, the invention will be described in the context of providing information regarding a status of an item being transported within a hospital facility.

Hospitals are required and or desire to track various items that are delivered internally from their internal service departments to various areas of the hospital, including but not limited to, nursing units, patients, ancillary and support areas, surgical and emergency areas, outpatient areas and clinics. Typical examples of this would be the delivery of medication to nursing units, the picking up of lab specimens from nursing areas, the delivery or pick up of blood products from the blood bank, etc. Many of the deliveries may require tracking and security for regulatory purposes, such as the delivery and storage of controlled substances by the pharmacy or the delivery and storage of blood products from the blood bank. In other instances the tracking and security are highly desirable, such as the delivery of high cost or high alert (e.g., dangerous) medications.

Currently, hospital personnel who wish to accurately ascertain the status of a particular item have to place telephone calls, ask other personnel, walk the planned delivery route, etc. to accurately ascertain the status of the item. For example, to accurately ascertain the status of a medication package which has been sent out from the hospital pharmacy for delivery to a particular nursing unit, hospital personnel may first need to contact the nursing unit to confirm that the medication package was delivered. If the medication package has not yet been delivered, hospital personnel may need to contact the person who was making the delivery. If the person making the delivery is not responsive, hospital personnel may need to walk the planned delivery route to try to find the current location of the medication package.

Having to take the above-described actions to accurately ascertain the status of an item is labor intensive, relatively expensive, prone to inaccuracies, and thus less than optimal.

BRIEF DESCRIPTION OF THE DRAWINGS

Various embodiments of the invention are described herein in by way of example in conjunction with the following figures, wherein like reference characters designate the same or similar elements.

FIGS. 6-16 are exemplary screen shots of web pages generated by the system of FIG. 1.

DETAILED DESCRIPTION

It is to be understood that at least some of the figures and descriptions of the invention have been simplified to illustrate elements that are relevant for a clear understanding of the invention, while eliminating, for purposes of clarity, other elements that those of ordinary skill in the art will appreciate may also comprise a portion of the invention. However, because such elements are well known in the art, and because they do not facilitate a better understanding of the invention, a description of such elements is not provided herein.

As described in more detail hereinbelow, aspects of the invention may be implemented by a computing device and/or a computer program stored on a computer-readable medium. The computer-readable medium may comprise a disk, a device, and/or a propagated signal.

Figure 1:
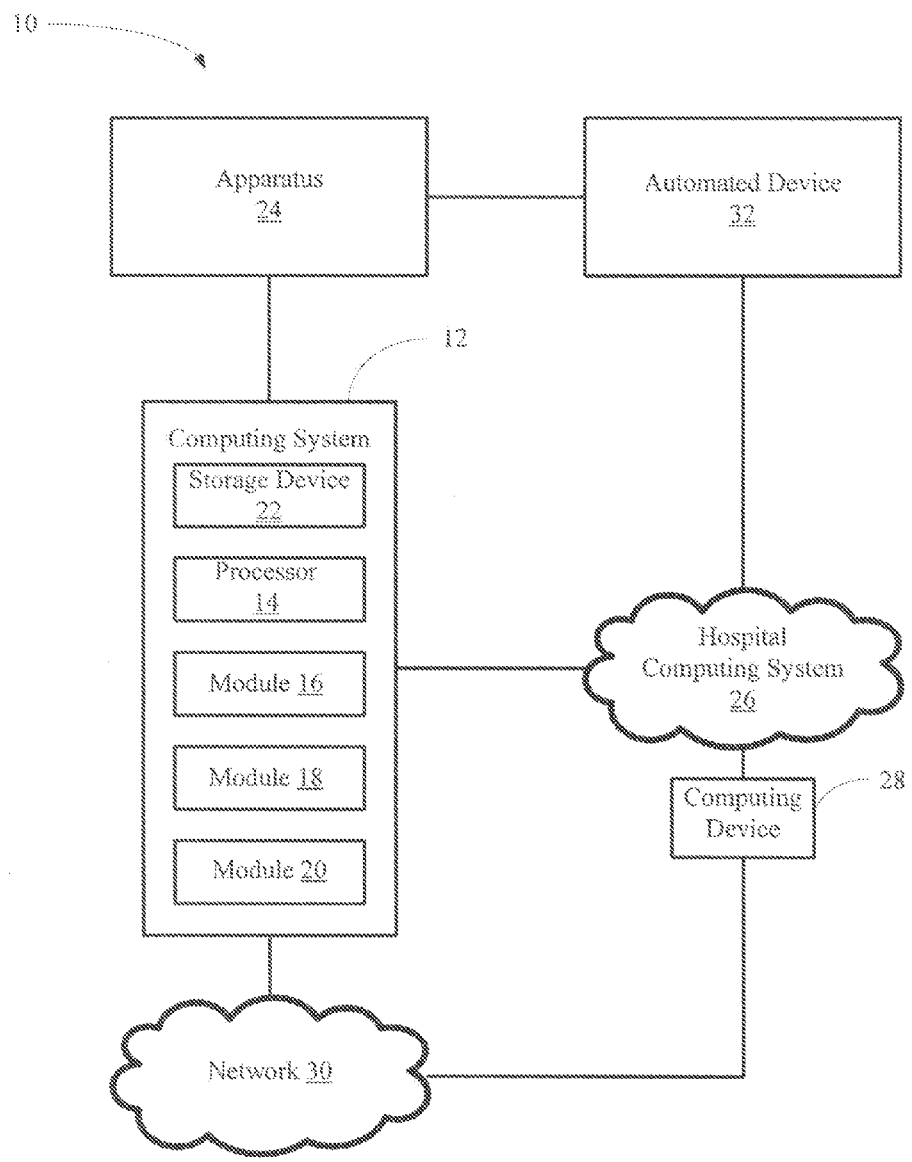
FIG. 1 illustrates various embodiments of a system.

FIG. 1 illustrates various embodiments of a system 10. The system 10 may be utilized to provide information regarding a status of an item. The information may be provided for a variety of different items, and may relate to items being securely transported from a first location within an environment to a second location within the environment. Such items may include, for example, medicines, lab specimens, blood products, etc., and the environment may be a hospital. Thus, it will be appreciated that the system 10 may be utilized, for example, to provide information regarding a status of a medication package sent from a hospital pharmacy to a nursing unit of the hospital. It will also be appreciated that such information may be utilized to establish a chain of custody record for the items.

The system 10 includes a computing system 12. The computing system 12 may be embodied as any suitable type of computing device (e.g., a server, a desktop, a laptop, etc.) that includes a processor 14. The computing system 12 also includes a first module 16 communicably connected to the processor 14, a second module 18 communicably connected to the processor 14, and a third module 20 communicably connected to the processor 14. The first, second and third modules 16-20 will be described in more detail hereinbelow. According to various embodiments, the computing system 12 also includes a storage device 22 communicably connected to the processor 14. The storage device 22 may be configured to store information in an organized manner such as a database. Various embodiments of the computing system 12 are described in more detail hereinbelow with respect to FIG. 2.

The computing system 12 is wirelessly connected to an apparatus 24. According to various embodiments, the apparatus 24 comprises a portion of the system 10. The apparatus 24 may be utilized to securely transport items throughout an environment. For example, the apparatus 24 may be utilized to securely transport medicines, lab specimens, blood products, food, general supplies, mail, etc. throughout a hospital. Although the apparatus 24 may be utilized to transport a variety of different items throughout a variety of different types of facilities, for purposes of simplicity, the apparatus 24 will be described in the context of transporting medicines throughout a hospital facility. Various embodiments of the apparatus 24 are described in more detail hereinbelow with respect to FIGS. 3-5. Although only one apparatus 24 is shown in FIG. 1, it will be appreciated that the computing system 12 may be wirelessly connected to any number of apparatuses 24, and that any number of apparatuses 24 may comprise a portion of the system 10.

According to various embodiments, the computing system 12 is also communicably connected to a hospital computing system 26, and to a computing device 28 via the hospital computing system 26 or via a network 30. The computing system 12 may be communicably connected to the hospital computing system 26 via any combination of wired and wireless pathways. The computing device 28 may be any suitable type of computing device (e.g., a server, a desktop, a laptop, etc.), and is generally accessible by an authorized employee of the hospital. Although only one computing device 28 is shown in FIG. 1, it will be appreciated that the computing system 12 may be communicably connected to any number of such computing devices 28.

The network 30 may include any type of delivery system including, but not limited to, a local area network (e.g., Ethernet), a wide area network (e.g. the Internet and/or World Wide Web), a telephone network (e.g., analog, digital, wired, wireless, PSTN, ISDN, GSM, GPRS, and/or xDSL), a packet-switched network, a radio network, a television network, a cable network, a satellite network, and/or any other wired or wireless communications network configured to carry data. The network 30 may include elements, such as, for example, intermediate nodes, proxy servers, routers, switches, and adapters configured to direct and/or deliver data. In general, the computing system 12 may be structured and arranged to communicate with the computing device 28 via the network 30 using various communication protocols (e.g., HTTP, TCP/IP, UDP, WAP, WiFi, Bluetooth) and/or to operate within or in concert with one or more other communications systems.

According to various embodiments, the apparatus 24 may also be wirelessly connected to an automated device 32, and the automated device 32 may also be communicably connected to the hospital computing system 26. The automated device 32 may be communicably connected to the hospital computing system 26 via any combination of wired and wireless pathways. The automated device 32 may be, for example, an automated dispensing cabinet (ADC) having a number of locked drawers, and one or more of the drawers of the ADC may be unlocked based on instructions transmitted by the apparatus 24 and/or inputs entered by a hospital employee. Although only one automated device 32 is shown in FIG. 1, it will be appreciated that the apparatus 24 may be wirelessly connected to any number of such automated devices 32.

The first module 16 of the computing system 12 is configured to receive chain of custody information transmitted from the apparatus 24. The chain of custody information includes item information, identification information and location information. Item information includes, for example, a name of an item (e.g., Hydromorphone PCA), an amount of the item (e.g., 20 mg/ml), a time when the item was placed into a secured area of the apparatus 24, a time when the item was removed from the apparatus 24, etc. Identification information includes, for example, a name of a person who gained access to the item, a time when the person gained the access, etc. Location information includes, for example, a location of the apparatus 24 (e.g., a starting location, a destination location, one or more intermediate locations) within the facility, a time when the apparatus 24 is at the starting location, a time when the apparatus 24 is at the destination location, a time when the apparatus 24 is at an intermediate location, etc. The information received by the first module 16 is stored at the storage device 22, and may be organized in the form of a database.

The second module 18 of the computing system 12 is configured to determine a status of an item based on the chain of custody information. For example, the second module 18 may determine that the item is "waiting to be delivered", "in transit", "delivered", etc. The "waiting to be delivered" status may be determined based on chain of custody information which indicates that the item was removed from the pharmacy, that the item was placed into a particular secured area of the apparatus 24, and that the apparatus 24 is at a staring location of a delivery route. The delivery route may be from a starting point to a first destination point, from a starting point to a first destination point to a second destination point, from a starting point to a first destination point to a second destination point and back to the starting point, etc.

The "waiting to be delivered" status may also include the name of the person who removed the item from the pharmacy, the time the item was removed from the pharmacy, the name of the person who placed the item into the secured area of the apparatus 24, the time the item was placed into the secured area of the apparatus 24, the planned destination of the apparatus 24, etc.

The "in transit" status may be determined based on chain of custody information which indicates that the apparatus 24 has started its delivery route but has not yet reached its intended destination. The "in transit" status may also include the "waiting to be delivered" information as well as the departure time of the apparatus 24, the estimated arrival time of the apparatus 24 at the intended destination, etc.

The "delivered" status may be determined based on chain of custody information which indicates that the apparatus 24 has reached the intended destination and that the item has been removed from the apparatus 24. The "delivered" status may also include the "waiting to be delivered" information and the "in transit" information as well as the arrival time of the apparatus 24 at the intended destination, the name of the person who removed the item from the apparatus 24, the estimated time until the apparatus 24 returns to the starting location, etc.

The status information determined by the second module 18 is stored at the storage device 22. As the apparatus 24 may securely transport a plurality of items within the facility at a given time, with different starting locations and/or destination locations for different items, it will be appreciated that the chain of custody information and the status information for the respective items may be organized in a relational database whereby all of the chain of custody information and status information associated with items being transported by the apparatus 24 are related to the apparatus 24 in the database. For example, the information applicable to the apparatus 24 may include the chain of custody information and the status information for each item being transported by the apparatus 24. Also, for embodiments where the system 10 includes more than one apparatus 24, the chain of custody information and the status information may be organized on an apparatus by apparatus basis.

The third module 20 of the computing system 12 is configured to arrange data in a specified format, wherein the data includes the chain of custody information and the status information. The third module 20 is also configured to transmit the data. According to various embodiments, the data is transmitted to an authorized computing device (e.g., computing device 28). According to various embodiments, the third module 20 is configured as a web-based user interface which permits an authorized user to request the data which includes the chain of custody information and the status information, retrieves the requested data from the database, places the retrieved data into a web page, and transmits the web page including the chain of custody information and the status information to the computing device 28 for presentation to the authorized user. FIGS. 6-16 are exemplary screen shots of web pages generated by the system 10. Although the user interface may be a web-based user interface, the request for and the transmission of the data may be effectuated either via the network 30 or via a local area network connecting the computing system 12 to the hospital computing system 26.

The first, second and third modules 16-20 are communicably connected to one another, and may be implemented in hardware, firmware, software and combinations thereof. For embodiments utilizing software, the software may utilize any suitable computer language (e.g., C, C++, Java, JavaScript, Visual Basic, VBScript, Delphi) and may be embodied permanently or temporarily in any type of machine, component, physical or virtual equipment, storage medium, or propagated signal capable of delivering instructions to a device. The modules 16-20 (e.g., software application, computer program) may be stored on a computer-readable medium (e.g., disk, device, and/or propagated signal) such that when a computer reads the medium, the functions described herein are performed.

For embodiments where the computing system 12 includes more than one computing device, the modules 16-20 may be distributed across a plurality of computing devices. According to various embodiments, the functionality of the modules 16-20 may be combined into fewer modules (e.g., a single module).

Figure 2:
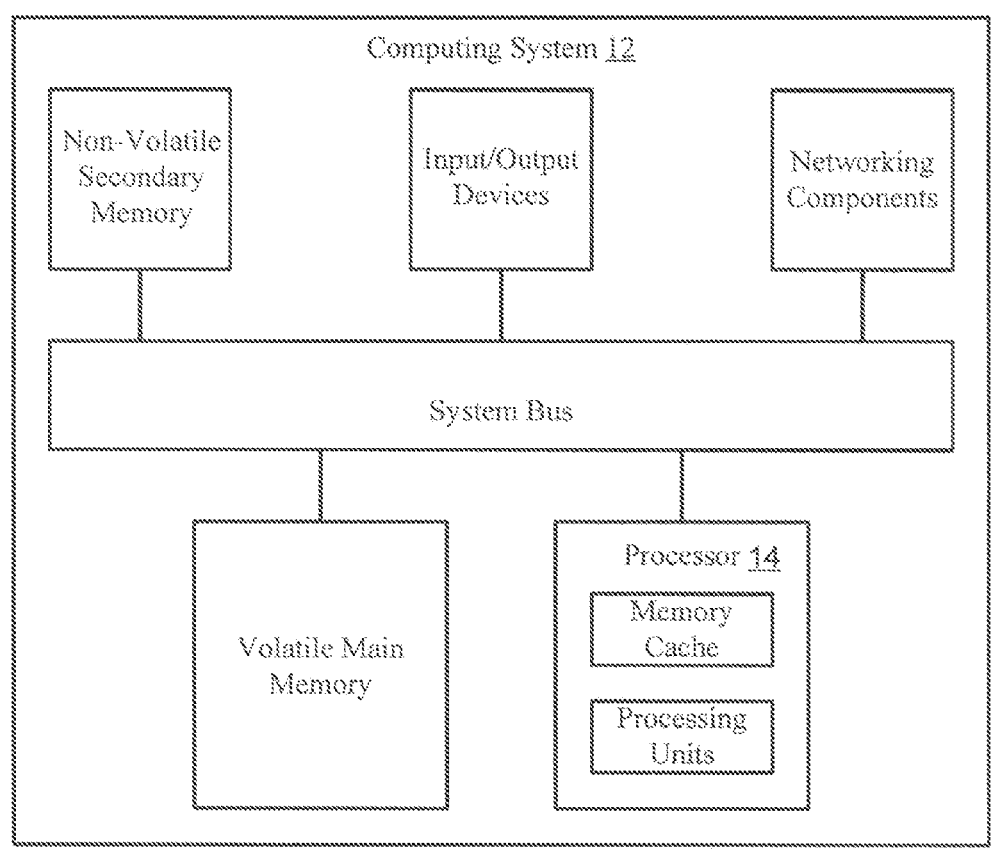
FIG. 2 illustrates various embodiments of a computing system of the system of FIG. 1.

FIG. 2 illustrates various embodiments of the computing system 12. The computing system 12 may be embodied as one or more computing devices, and includes networking components such as Ethernet adapters, non-volatile secondary memory such as magnetic disks, input/output devices such as keyboards and visual displays, volatile main memory, and a processor 14. Each of these components may be communicably connected via a common system bus. The processor 14 includes processing units and on-chip storage devices such as memory caches.

According to various embodiments, the computing system 12 includes one or more modules (e.g., modules 16-20) which are implemented in software, and the software is stored in non-volatile memory devices while not in use. When the software is needed, the software is loaded into volatile main memory. After the software is loaded into volatile main memory, the processor 14 reads software instructions from volatile main memory and performs useful operations by executing sequences of the software instructions on data which is read into the processor 14 from volatile main memory. Upon completion of the useful operations, the processor 14 writes certain data results to volatile main memory.

Figure 3:
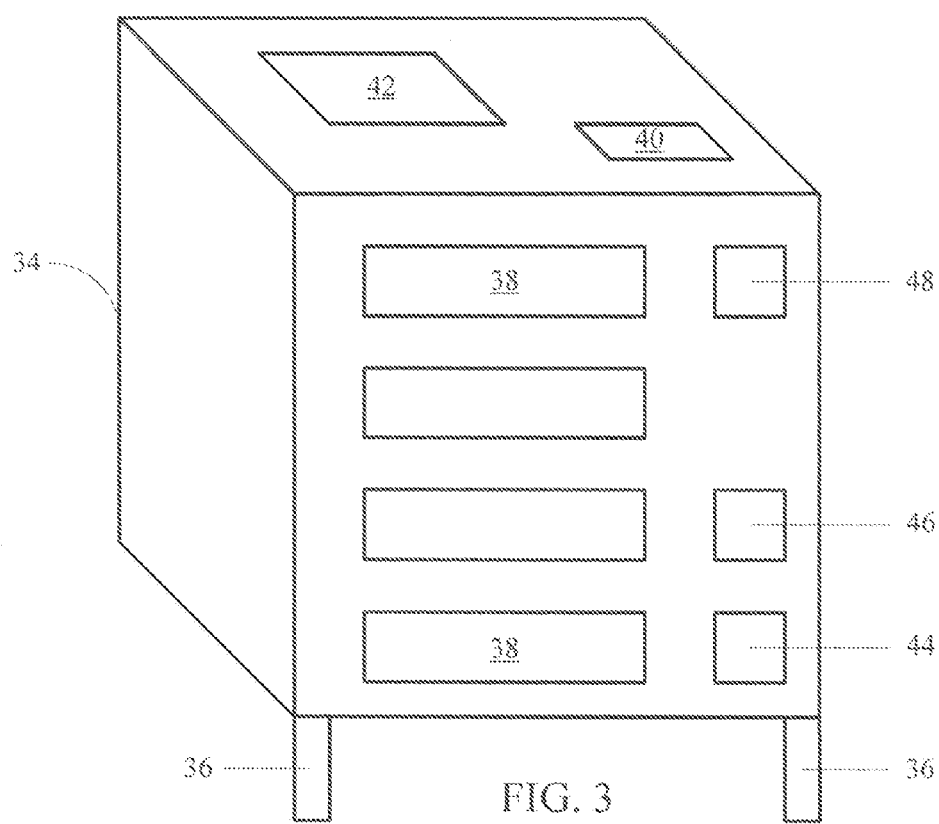
FIG. 3 illustrates various embodiments of an apparatus of the system of FIG. 1.

FIG. 3 illustrates various embodiments of the apparatus 24, where the apparatus 24 is embodied as a cart 34. The cart 34 may be any suitable type of cart utilized to securely transport items such as medicines, lab specimens, blood products, food, general supplies, mail, etc. throughout an environment. The cart 34 includes first and second wheels 36, a plurality of storage areas 38, an input device 40 such as, for example, a keypad, a biometric reader, etc. and a passive radio frequency identification (RFID) tag reader 42. Although not shown in FIG. 3, the cart 34 may also include a battery and a computing device.

In general, one or more of the storage areas 38 are normally secured (e.g., closed and locked), and such secure storage areas 38 may hold one or more items to be delivered to throughout the facility. For example, the secure storage areas 38 may hold one or more medicines to be delivered to ADCs positioned throughout a hospital. At least some of the items may be packaged (e.g., medicines packaged in individual unit dose packages), and such packages may have RFID tags embedded therein. Alternatively, such packages may have one or more bar codes printed thereon. An authorized person may position a hospital issued passive radio frequency identification (RFID) tag proximate the first passive tag reader 42 and/or use the input device 40 to enter a specific code, enter a biometric identification, etc. to cause one or more of the secure storage areas 38 to open, thereby gaining access to the items held by the secure storage areas 38.

According to various embodiments, the cart 34 also includes a second passive RFID tag reader 44. The second passive RFID tag reader 44 may be positioned at any number of suitable locations on or in the cart 34. When an item (e.g., a medication package) embedded with an RFID tag is placed into or removed from one of the secure storage areas 38 of the cart 34, the second passive RFID tag reader 44 is operative to identify the item as it is removed.

According to other embodiments, the cart 34 also includes a bar code reader 46. The bar code reader 46 may be positioned at any number of suitable locations on the cart 34. When an item (e.g., a medication package) having a bar code printed thereon is removed from one of the secure storage areas 38 of the cart 34, the person who removed the item may utilize the bar code reader 46 to read the bar code on the removed item. The reading of the bar code is operative to identify the removed item.

According to various embodiments, the cart 34 also includes an interface 48. The interface 48 may be positioned at any number of locations in or on the cart 34. The interface 48 is configured to wirelessly communicate with one or more automated devices such as, for example, a mobile robot, automated secure cabinets, etc. The automated secure cabinets may include, for example, an ADC, an automated refrigeration unit, an automated bay of a tube station, etc. The interface 48 may be utilized to operate at least some of the functionality of the automated secure cabinets. For some embodiments, when the cart 34 is proximate an ADC, the interface 48 may transmit an instruction to the ADC to display a list of medication packages which need to be replenished at the ADC. This automatic process eliminates the need for a hospital employee to advance through the user screens of the ADC to display the list. In addition, the interface 48 may receive the list from the ADC, and operate to unlock the secure storage area 38 which holds the first medication package on the list, thereby providing an authorized hospital employee access to the needed medication package.

Figure 4:
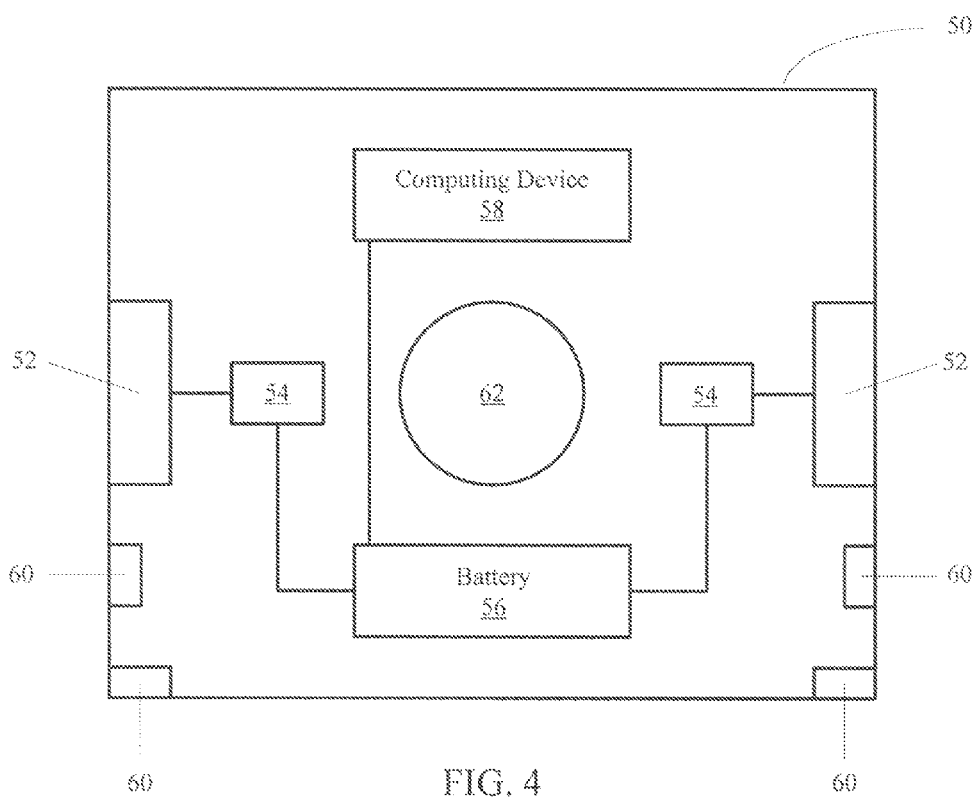
FIG. 4 illustrates other embodiments of the apparatus of FIG. 3.

FIG. 4 illustrates various embodiments of the apparatus 24, where the apparatus 24 is embodied as a mobile robot 50. The mobile robot 50 may be any suitable type of mobile robot. For example, according to various embodiments, the mobile robot 50 may be configured similar to the robot described in U.S. Pat. Nos. 6,046,565 and 7,100,725, the contents of which are hereby incorporated by reference. As shown in FIG. 4, according to various embodiments, the mobile robot 50 includes first and second wheels 52, first and second motors 54 mechanically coupled to the respective first and second wheels 52, a battery 56 electrically connected to the first and second motors 54, a computing device 58 connected to the battery 56, and a plurality of sensors 60 coupled to the computing device 58. The computing device 58 includes a processor. For purposes of clarity, the processor, and the electrical connections between the respective sensors 60 and the computing device 58 are not shown in FIG. 4.

According to various embodiments, the mobile robot 50 also includes a receptacle 62 configured for receiving a post 64 (see FIG. 5) which couples the mobile robot 50 and the cart 34 to one another. The receptacle 62 may be configured to mechanically and electrically couple the mobile robot 50 and the cart 34 to one another when the post 64 is received by the receptacle 62. Aspects of the mobile robot 50 may be implemented by the computing device 58 and/or a computer program stored on a computer-readable medium. The computer-readable medium may comprise a disk, a device, and/or a propagated signal.

Figure 5:
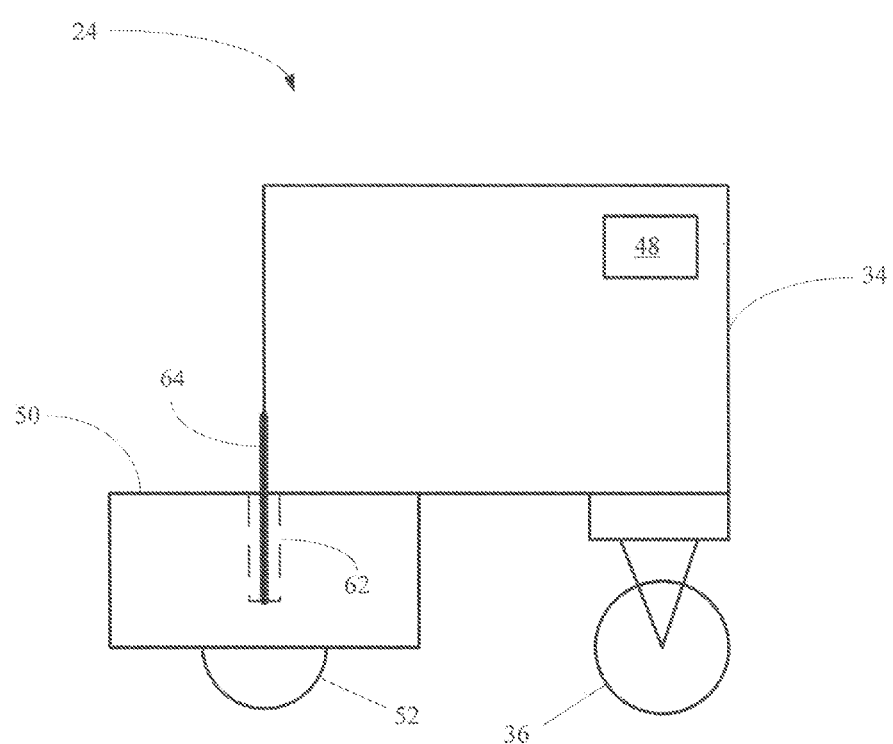
FIG. 5 illustrates yet other embodiments of the apparatus of FIG. 3.
Figure 6:
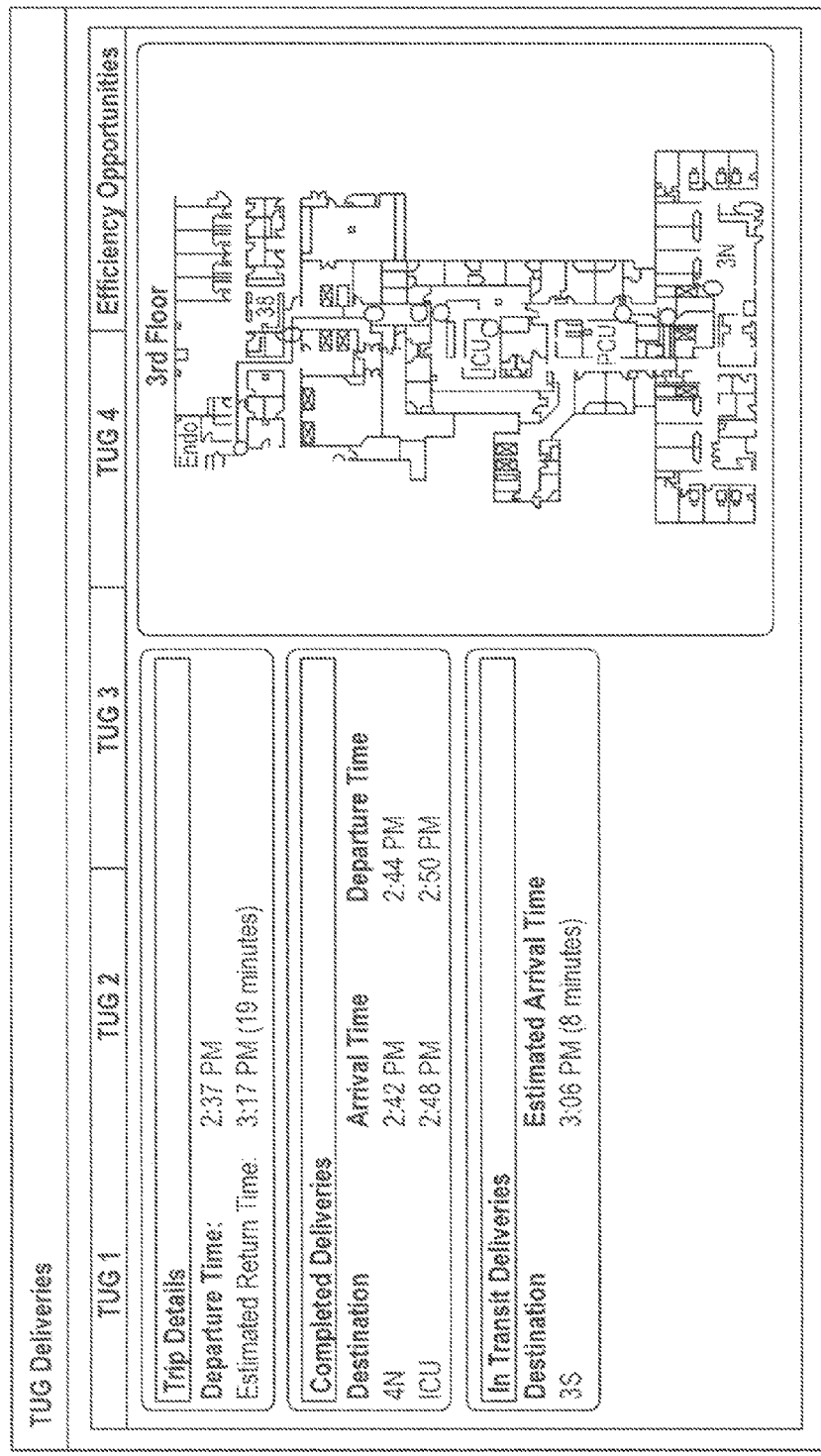
Figure 7:
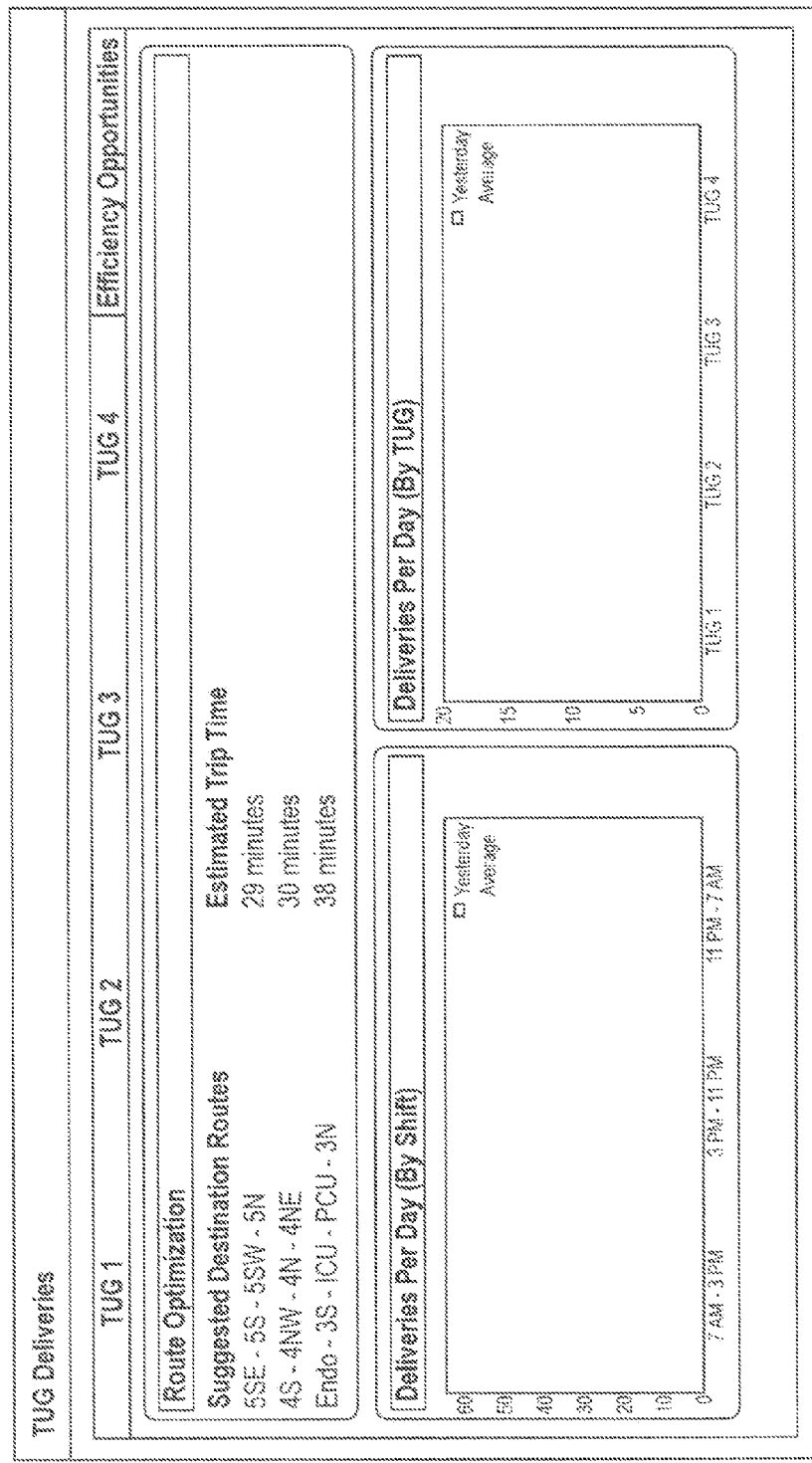

FIG. 5 illustrates yet other embodiments of the apparatus 24, where the apparatus 24 is embodied by the cart 34 and the mobile robot 50 coupled to one another via the post 64 and the receptacle 62. The mobile robot 50 navigates throughout the facility and pushes or pulls the cart 34 along therewith. For such embodiments, the cart 34 is communicably connected to the computing device 58 of the mobile robot 50, and the cart 34 may utilize the battery 56 and the computing device 58 of the mobile robot 50. As indicated hereinabove, according to various embodiments, the cart 34 includes the interface 48. Therefore, according to various embodiments, the apparatus 24 includes the cart 34, the interface 48 and the mobile robot 50. For such embodiments, the interface 48 may be communicably connected to the computing device 58 of the mobile robot 50, and the interface 48 may utilize the battery 56 and the computing device 58 of the mobile robot 50.

With respect to the operation of the apparatus 24, the apparatus 24 is configured to transmit location information associated with the apparatus 24 to the computing system 12. According to some embodiments, the location information is transmitted continuously between a first position (e.g., a starting position for a given delivery route) and a second position (e.g., a destination of the given delivery route). According to other embodiments, the location information is transmitted intermittently. The apparatus location information may be determined in any suitable manner. For example, according to various embodiments, the apparatus 24 may automatically determine its location based on a map stored at the apparatus 24. According to other embodiments, the apparatus 24 may determine its location based on certain landmarks within the hospital. According to yet other embodiments, the apparatus 24 may determine its location within a hospital based on its passing RFID readers positioned throughout a hospital. The transmitted apparatus location information may also include the time when the location information was determined.

Also, prior to a person placing the item into a secure storage area 38 of the cart 34, the apparatus 24 captures identification information associated with the person and transmits the identification information to the computing system 12. The identification information may be captured based on the person's passive RFID tag coming in proximity to the first RFID tag reader 42, by the person subjecting a portion of their body (e.g., a thumb) to a biometric reader, by a code entered via the input device 40, etc. The transmitted identification information may also include the time when the identification information was captured.

Additionally, as the item is placed into the secure storage area 38 of the cart 34, item information is captured by the second passive RFID tag reader 44. Alternatively, prior to the person placing the item into the secure storage area 38 of the cart 34, the person may utilize the bar code reader 46 to scan a bar code positioned on the item or on a package containing the item. The transmitted item information may also include the time when the item information was captured.

Similarly, once the apparatus 24 has reached the destination for the item being delivered, the apparatus 24 may determine its location information, the apparatus 24 may capture the identification information associated with the person removing the item from the secured storage area 38 of the cart 34, and the apparatus 24 may capture the item information as the item is removed. The apparatus 24 transmits all such information to the computing system 12, and all such information may include the time when the information was determined and/or captured by the apparatus 24.

As described in more detail hereinafter, the information transmitted from the apparatus 24, including the location of the apparatus 24 within the facility, the person who gained access to the secured item, the time the person gained access to the secured item, the type of item removed, the time item was removed, etc. may be utilized by the computing system 12 to establish a chain of custody record for the item, and to determine a status of the item based on the chain of custody record for the item.

For embodiments where the apparatus 24 is embodied as the cart 34, the cart 34 may be utilized to deliver items (e.g., medications) to specific locations or to devices other than an ADC. In such embodiments, the cart 34 may be manually pushed or pulled from one location to another within the facility, and the apparatus 24 retains functionality for establishing a chain of custody for medications loaded onto or off of the cart 34.

For embodiments where the apparatus 24 is embodied as the cart 34 with the interface 48, the cart 34 may be manually pushed or pulled from one location within the facility to another location within the facility, and the apparatus 24 retains all of the other functionalities described above. Therefore, this embodiment of the apparatus 24 may be utilized to help establish the chain of custody record.

Figure 17:
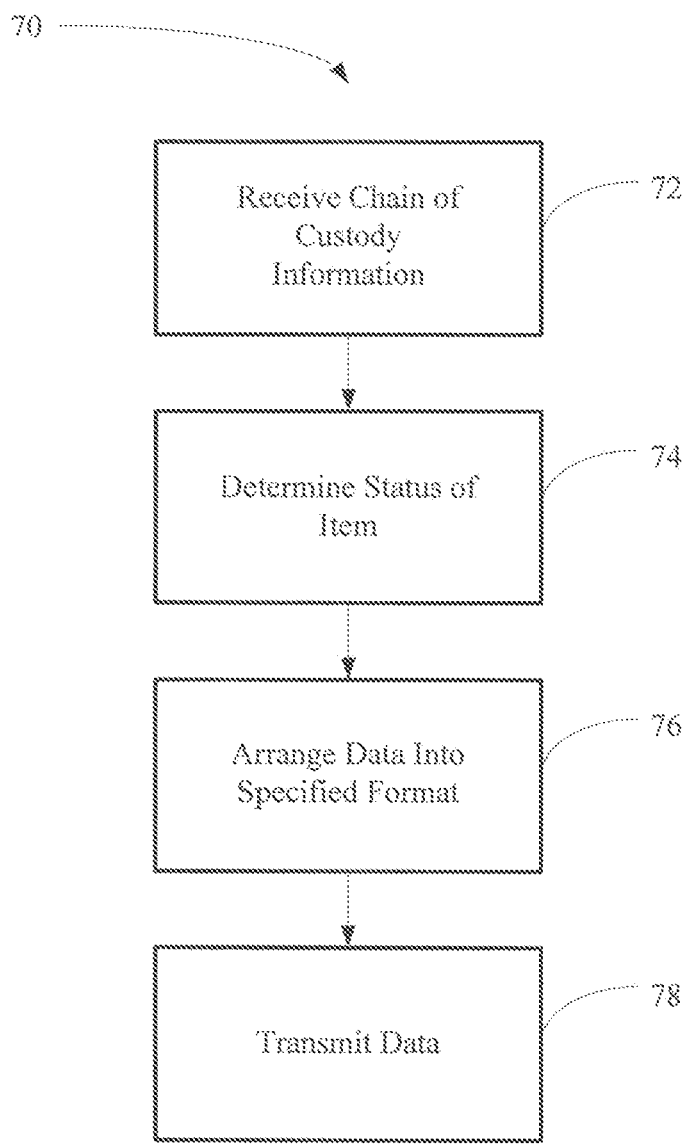
FIG. 17 illustrates various embodiments of a method.

FIG. 17 illustrates various embodiments of a method 70. As explained in more detail hereinbelow, the method 70 may be utilized to provide information regarding a status of an item. According to various embodiments, the method 70 may be implemented by the system 10 of FIG. 1. For purposes of simplicity, the method 70 will be described in the context of its implementation by the system 10. However, it will be appreciated that the method 70 may be implemented by any number of different systems.

The process starts at block 72, where the computing system 12 receives chain of custody information from the apparatus 24, wherein the chain of custody information is associated with an item. According to various embodiments, the computing system 12 also stores the received chain of custody information at the storage device 22. The computing system 12 may receive any amount of such chain of custody information from any number of apparatuses 24, and the received chain of custody information is stored at the storage device 22.

From block 72, the process advances to block 74, where the computing system 12 determines a status of the item based on the chain of custody information. According to various embodiments, the computing system 12 also stores the determined status information at the storage device 22. For instances where the received chain of custody information is for more than one item, the computing system 12 determines the status of each item.

From block 74, the process advances to block 76, where the computing system 12 arranges data into a specified format, wherein the data includes the chain of custody information and the status information. The specified format may be HTML, XML, XHTML, etc.

From block 76, the process advances to block 78, where the computing system 12 transmits the data to an authorized computing device (e.g., computing device 28). The computing system 12 may transmit the data in accordance with any suitable transmission protocol. For example, according to various embodiments, the computing system 12 transmits the data in accordance with the HTTP transmission protocol. According to various embodiments, the computing system 12 may transmit the data to any number of authorized computing devices. The process described from blocks 72-76 may be repeated any number of times.

Nothing in the above description is meant to limit the invention to any specific materials, geometry, or orientation of elements. Many part/orientation substitutions are contemplated within the scope of the invention and will be apparent to those skilled in the art. The embodiments described herein were presented by way of example only and should not be used to limit the scope of the invention.

Although the invention has been described in terms of particular embodiments in this application, one of ordinary skill in the art, in light of the teachings herein, can generate additional embodiments and modifications without departing from the spirit of, or exceeding the scope of, the described invention. Accordingly, it is understood that the drawings and the descriptions herein are proffered only to facilitate comprehension of the invention and should not be construed to limit the scope thereof.

What is claimed is:

1. A system, comprising:
   an apparatus, comprising:
   a cart; and
   an interface connected to the cart,
   wherein the interface is configured to wirelessly communicate with at least one automated device, wherein the at least one automated device comprises at least one automated medicine dispenser,
   wherein when the cart is proximate to the at least one automated device, the interface transmits an instruction to the automated device to display a list of items that requires replenishment,
   wherein the apparatus is configured for transporting an item from a first location to a second location within a facility, wherein the item comprises a medication, and
   a computing system wirelessly connected to the apparatus, wherein the computing system comprises:
   a processor;
   a first module communicably connected to the processor, wherein the first module is configured for receiving, from the apparatus, chain of custody information associated with the item and the apparatus, wherein the chain of custody information comprises: (a) item information identifying the item being transported by the apparatus; (b) identification information identifying one or more persons who gained access to the item; and (c) location information associated with the apparatus which transports the item from the first location to the second location, wherein the location information comprises one or more locations of the apparatus within the facility as it transports the item between the first and second locations, wherein the location information is determined by the apparatus;
   a second module communicably connected to the processor, wherein the second module is configured for determining a delivery status of the item based on the received chain of custody information, wherein the delivery status comprises:
   waiting at the first location to be delivered at a first point in time;
   in transit between the first and second locations at a second point in time; and
   delivered to the second location at a third point in time; and
   a third module communicably connected to the processor, wherein the third module is configured for:
   arranging data into a specified format, wherein the data comprises the delivery status of the item and the chain of custody information; and
   transmitting the data.

2. The system of claim 1, wherein the item information further comprises an amount of the item.

3. The system of claim 1, wherein the identification information further comprises a time the one or more persons gained access to the item.

4. The system of claim 1, wherein the location information further comprises at least one of the following:
   the first location of the apparatus;
   the second location of the apparatus;
   a first time when the apparatus starts moving away from the first location; and
   a second time when the apparatus arrives at the second location.

5. The system of claim 1, wherein the computing system further comprises a storage device communicably connected to the processor.

6. The system of claim 1, wherein the apparatus is configured for securely transporting the item from the first location to the second location.

7. The system of claim 1, wherein the apparatus comprises:
   a mobile robot coupled to the cart and communicably connected to the interface.

8. The system of claim 7, wherein the interface is configured to wirelessly communicate with the mobile robot.

9. A method, comprising:
   providing an apparatus for transporting an item from a first location to a second location within a facility, the apparatus transmitting chain of custody information associated with the item and the apparatus, wherein the item comprises a medication;
   receiving, at a first module of a computing device wirelessly connected to the apparatus, the transmitted chain of custody information associated with the item and the apparatus, wherein receiving the chain of custody information comprises receiving: (a) item information identifying the item being transported by the apparatus; (b) identification information identifying one or more persons who gained access to the item; and (c) location information associated with the apparatus which transports the item from the first location to the second location, wherein receiving the location information comprises receiving one or more locations of the apparatus within the facility as it transports the item between the first and second locations, wherein the location information is determined by the apparatus;
   determining, at a second module of the computing device, a delivery status of the item based on the chain of custody information, wherein the delivery status comprises:
   waiting at the first location to be delivered at a first point in time;
   in transit between the first and second locations at a second point in time; and
   delivered to the second location at a third point in time;
   arranging, at a third module of the computing device, data into a specified format, wherein the data comprises the delivery status of the item and the chain of custody information;
   transmitting, at a third module of the computing device, the data from the computing device; and transmitting a wireless communication from an interface of the apparatus to at least one automated device when the apparatus is proximate to the at least one automated device, wherein the at least one automated device comprises at least one automated medicine dispenser, and wherein the wireless communication is an instruction to display a list of items that requires replenishment.

10. The method of claim 9, wherein receiving the item information comprises receiving an amount of the item.

11. The method of claim 9, wherein receiving the identification information comprises receiving a time the one or more persons gained access to the item.

12. The method of claim 9, wherein receiving the location information further comprises receiving at least one of the following:
- the first location of the apparatus;
- the second location of the apparatus;
- a first time when the apparatus starts moving away from the first location; and
- a second time when the apparatus arrives at the second location.

13. The method of claim 9, further comprising storing, at the computing device, the delivery status of the item and the chain of custody information.

14. The system of claim 1, wherein the at least one automated device is a lockbox.

15. The system of claim 8, wherein the at least one automated device is a lockbox.

16. The system of claim 1, wherein the apparatus automatically determines its location based on a map of the facility stored in the apparatus.

17. The system of claim 1, wherein the apparatus automatically determines its location based on certain landmarks within the facility.

18. The system of claim 1, wherein the apparatus automatically determines it location based on its passing RFID tags positioned throughout the facility.

19. The method of claim 9, wherein the apparatus automatically determines its location based on a map of the facility stored in the apparatus.

20. The method of claim 9, wherein the apparatus automatically determines its location based on certain landmarks within the facility.

21. The method of claim 9, wherein the apparatus automatically determines it location based on its passing RFID tags positioned throughout the facility.

\* \* \* \* \*